United States Patent
Ozeki et al.

(10) Patent No.: US 8,629,980 B2
(45) Date of Patent: Jan. 14, 2014

(54) OPTICAL MICROSCOPE AND OPTICAL INSTRUMENTATION

(75) Inventors: Yasuyuki Ozeki, Osaka (JP); Kazuyoshi Itoh, Osaka (JP); Fumihiro Dake, Osaka (JP); Kiichi Fukui, Osaka (JP); Shinichiro Kajiyama, Osaka (JP); Yuma Kitagawa, Osaka (JP); Norihiko Nishizawa, Osaka (JP); Kazuhiko Sumimura, Osaka (JP)

(73) Assignee: Canon Kabushiki Kaisha (JP)

( * ) Notice: Subject to any disclaimer, the term of this patent is extended or adjusted under 35 U.S.C. 154(b) by 0 days.

(21) Appl. No.: 13/375,388

(22) PCT Filed: Jun. 2, 2010

(86) PCT No.: PCT/JP2010/059327
§ 371 (c)(1),
(2), (4) Date: Feb. 16, 2012

(87) PCT Pub. No.: WO2010/140614
PCT Pub. Date: Dec. 9, 2010

(65) Prior Publication Data
US 2012/0140217 A1    Jun. 7, 2012

(30) Foreign Application Priority Data

Jun. 3, 2009   (JP) ................. 2009-134364
Nov. 20, 2009  (JP) ................. 2009-265514

(51) Int. Cl.
*G01J 3/44*      (2006.01)
(52) U.S. Cl.
USPC ........................................ 356/301
(58) Field of Classification Search
USPC ............................. 356/301, 72–73
See application file for complete search history.

(56) References Cited

U.S. PATENT DOCUMENTS

| 5,367,156 A | 11/1994 | Domon et al. |
| 2002/0167724 A1 | 11/2002 | Iketaki et al. |

(Continued)

FOREIGN PATENT DOCUMENTS

| JP | 63-114429 | 5/1988 |
| JP | 5-218806 | 8/1993 |

(Continued)

OTHER PUBLICATIONS

Dake, et al., "Principle confirmation of stimulated Raman scattering microscopy", Optics & Photonics Japan 2008, 5pC12, Nov. 2008, 300-301.

(Continued)

*Primary Examiner* — Gregory J Toatley
*Assistant Examiner* — Abdullahi Nur
(74) *Attorney, Agent, or Firm* — Rossi, Kimms & McDowell LLP

(57) ABSTRACT

The invention provides an optical microscope that prevents an increase in the complexity of the light source system and is equipped with optics readily capable of adequate operation even when the modulation frequency is increased in order to reduce the impact of the intensity noise of the laser, etc. This optical microscope 100 irradiates a sample 6 with a first train of optical pulses having a first optical frequency, which is generated by a first light source, and a second train of optical pulses having a second optical frequency, which is temporally synchronized with the first train of optical pulses and is generated by a second light source, and detects light scattered from the sample 6. The repetition frequency of the train of optical pulses generated by the first light source is an integral sub-multiple of the repetition frequency of the train of optical pulses generated by the second light source.

14 Claims, 11 Drawing Sheets

(56) References Cited

U.S. PATENT DOCUMENTS

| | | |
|---|---|---|
| 2006/0238745 A1 | 10/2006 | Hashimoto et al. |
| 2010/0046039 A1* | 2/2010 | Xie et al. ............ 358/471 |
| 2010/0134793 A1 | 6/2010 | Krishnamachari et al. |

FOREIGN PATENT DOCUMENTS

| | | |
|---|---|---|
| JP | 2002-107301 | 4/2002 |
| JP | 2002-520612 | 7/2002 |
| JP | 2002-286641 | 10/2002 |
| JP | 2004-109368 A | 4/2004 |
| JP | 2005-062155 | 3/2005 |
| JP | 2007-250762 A | 9/2007 |
| JP | 2010-048805 | 3/2010 |
| WO | 00/04352 | 1/2000 |

OTHER PUBLICATIONS

Freudiger, et al., "Label-Free Biomedical Imaging with High Sensitivity by Stimulated Raman Scattering Microscopy", Science, 2008, vol. 322, No. 5909, 1857-1861.

Extended European Search Report for corresponding EP 10783396.4, mail date Feb. 7, 2013.

* cited by examiner

3 μm

10 μm

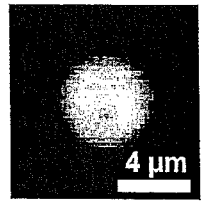
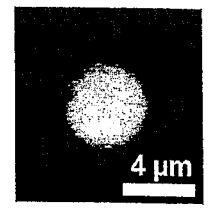
FIG. 8A                FIG. 8B
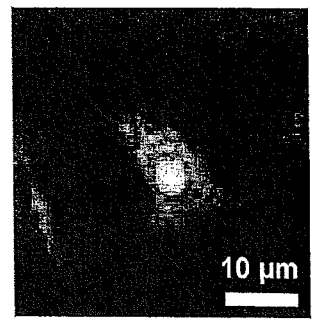
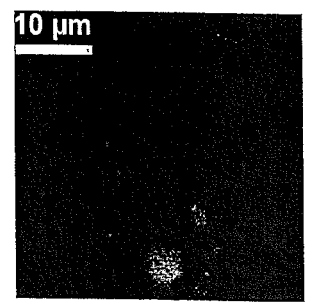
FIG. 9A                FIG. 9B

OPTICAL MICROSCOPE AND OPTICAL INSTRUMENTATION

TECHNICAL FIELD

The present invention relates to an optical microscope and optical instrumentation that can be used in a molecular vibrational imaging technique based on stimulated Raman scattering.

BACKGROUND ART

Microscopy utilizing the principle of Raman scattering has been expected to find application in the observation of cells in living organisms, etc., as a technique of molecular vibrational imaging that reflects molecular vibrational information.

Known microscopy techniques based on Raman scattering have heretofore included spontaneous Raman scattering microscopy and coherent anti-Stokes Raman scattering (CARS) microscopy.

In the former, the spectral information of the sample is acquired based on the fact that the frequency of the excitation light changes in accordance with the molecular vibrational frequency of the sample. However, since the resultant signal beam is extremely weak, improving the signal-to-noise (S/N) ratio has been a serious problem. On the one hand, in the latter, optical pulses of 2 colors ($\omega_{AS}$, $\omega_S$) are used to generate a CARS beam at a frequency ($2\omega_{AS}-\omega_S$) that is different from the excitation light. In CARS, the molecules are forced to oscillate, which has the advantage of obtaining a signal with a high S/N ratio. However, the problem is that the background presence of the so-called non-resonant signal, which is due to a non-linear response of electrons in the sample, degrades the contrast of the molecular vibrational images.

Stimulated Raman scattering (SRS) microscopy was proposed independently by the inventors (see Non-patent Document 1) and by Sunny Xie et al. of Harvard University (see Non-patent Document 2) as a way of addressing these contradictory problems of conventional Raman scattering microscopy.

The principle of stimulated Raman scattering microscopy is as follows.

Namely, the phenomenon of stimulated Raman scattering occurs at a focal spot when light is condensed on a sample in a state, in which one series of pulses of 2 colors ($\omega_{AS}$, $\omega_S$) is intensity-modulated, and the frequency difference between the 2 colors coincides with the molecular vibrational frequency of the sample at the focal spot. At such time, intensity modulation takes place in the excitation optical pulses that have not been intensity-modulated and the extent of intensity modulation due to the stimulated Raman scattering can be detected by photo-detecting the excitation light emitted from the sample. Therefore, molecular vibrational imaging of the sample is made possible based on the extent of the intensity modulation that takes place as a result of the stimulated Raman scattering.

FIG. 12 shows a block diagram of a conventional stimulated Raman scattering microscope used for principle confirmation.

As shown in FIG. 12, a conventional stimulated Raman scattering microscope 500 co-axially combines an anti-Stokes beam ($\omega_{AS}$), which is emitted from a titanium-sapphire laser 501, and a Stokes beam ($\omega_S$), which is emitted from an optical parametric oscillator 502 and intensity-modulated by an acousto-optic modulator (AOM) 503, with the help of a dichroic mirror 505 and condenses the beams through an objective lens 506 on a sample 507. At such time, scattered light is detected through an objective lens 508, a short-wave pass filter 509, and a focusing lens 510 using a photodiode (PD) 511 and a lock-in amplifier 512. It should be noted that the reference number 504 designates a mirror and the anti-Stokes beam ($\omega_{AS}$) has a repetition frequency of 76 MHz, a center wavelength of 765 nm, and a pulse width of 100 fs. In addition, the repetition frequency of the Stokes beam ($\omega_S$) is 76 MHz, its center wavelength 985-1005 nm, and its pulse width 200 fs. In addition, the frequency of the high-frequency signal source 513 is set to 2 MHz.

CITATION LIST

Non-Patent Documents

[Non-patent Document 1] Principle Confirmation of Stimulated Raman Scattering Microscopy, Fumihiro Dake, Yasuyuki Ozeki, Kazuyoshi Itoh, Optics & Photonics Japan, 2008, 5p C12, Nov. 5, 2008.

[Non-patent Document 2] Chiristian W. Freudiger, Wei Min, Brian G. Saar, Sijia Lu, Gary R. Holtom, Chengwei He, Jason C. That, Jing X. Kang, X. Sunny Xie, "Label-Free Biomedical Imaging with High Sensitivity by Stimulated Raman Scattering Microscopy (Label-Free High-Sensitivity Biomedical Imaging by Stimulated Raman Scattering Microscopy)", SCIENCE, Vol. 32, 219 December 2008, pp. 1857-1861.

DISCLOSURE OF INVENTION

Problem to be Solved by the Invention

However, the problem with the above-described conventional stimulated Raman scattering microscope is that the impact of the intensity noise of the laser serving as the light source degrades the S/N ratio. Additionally, another problem is the need for an acoustro-optic modulator used to modulate the intensity of the Stokes beam, which makes the system more complex.

Since the intensity noise of the laser decreases as the frequency becomes higher, raising the modulation frequency is effective in reducing the intensity noise of the laser. However, if the modulation frequency is increased, stricter requirements are imposed on the acoustro-optic modulator that performs intensity modulation and problems associated with increased system complexity become more pronounced. In addition, obtaining high-quality video images becomes more difficult when there are limitations imposed on raising the modulation frequency because of restrictions involved in the process of intensity modulation.

Thus, it is an object of the present invention to address the above-mentioned conventional problems and obtain an optical microscope that prevents an increase in the complexity of the light source system and is equipped with optics readily capable of adequate operation even when the modulation frequency is increased in order to reduce the impact of the intensity noise of the laser, etc.

Means for Solving Problem

In order to address the above-described problems, the inventive optical microscope is an optical microscope that irradiates a sample with a first train of optical pulses having a first optical frequency, which is generated by a first light source, and a second train of optical pulses having a second optical frequency, which is temporally synchronized with the first train of optical pulses and is generated by a second light source, and detects light scattered from the sample, wherein the repetition frequency of the train of optical pulses generated by the first light source is an integral sub-multiple of the repetition frequency of the train of optical pulses generated by the second light source.

Effects of the Invention

In the inventive optical microscope, the elements used for intensity modulation in conventional optical microscopes are not required, which simplifies the system of the optical microscope. In addition, the modulation frequency of the light pulse trains is set to a high value, which makes it possible to obtain images with a high S/N ratio.

BRIEF DESCRIPTION OF DRAWINGS

FIG. 8 A diagram illustrating differences between molecular vibrational images obtained by a stimulated Raman scattering microscope when the lock-in frequencies are different. FIG. 8(a) is a molecular vibrational image of a polystyrene bead obtained when the lock-in frequency is 2 MHz, and FIG. 8(b) is a molecular vibrational image of a polystyrene bead obtained when the lock-in frequency is 10 MHz.

FIG. 9 A diagram illustrating differences between molecular vibrational images obtained by a stimulated Raman scattering microscope when the lock-in frequencies are different. FIG. 9(a) is a molecular vibrational image of a plant cell obtained when the lock-in frequency is 2 MHz, and FIG. 9(b) is a molecular vibrational image of a plant cell obtained when the lock-in frequency is 10 MHz.

DESCRIPTION OF THE INVENTION

Figure 1:
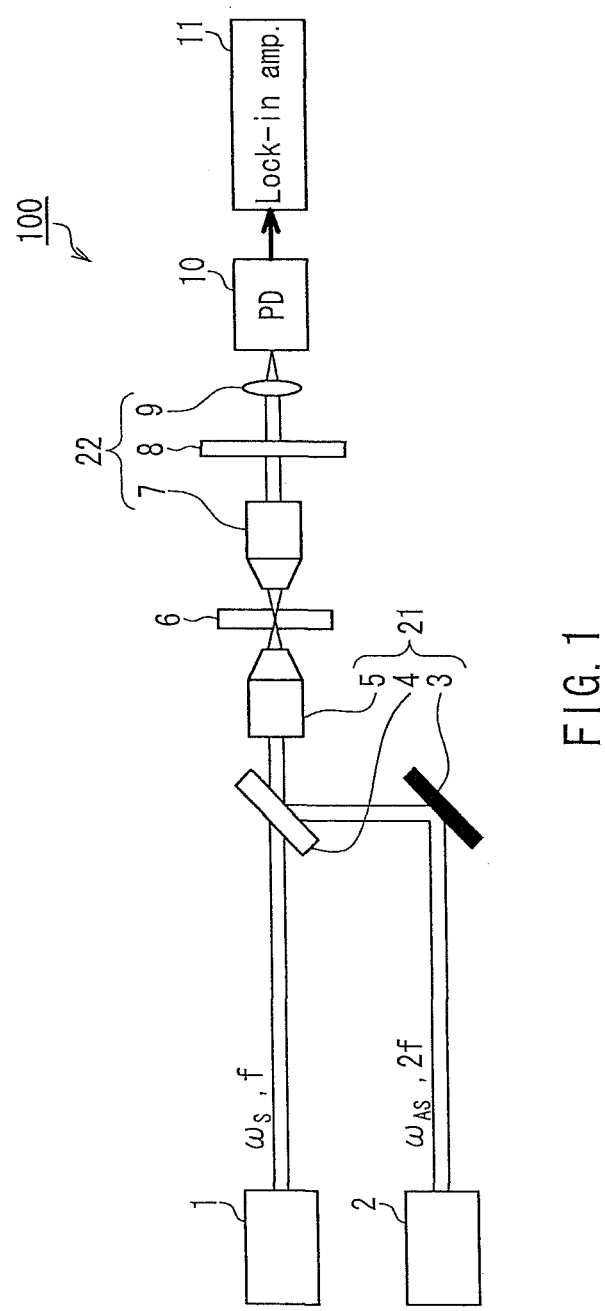
FIG. 1 A block diagram illustrating an overview of the optical microscope according to the first embodiment of the present invention.

The inventive optical microscope is an optical microscope that irradiates a sample with a first train of optical pulses having a first optical frequency, which is generated by a first light source, and a second train of optical pulses having a second optical frequency, which is temporally synchronized with the first train of optical pulses and is generated by a second light source, and detects light scattered from the sample, wherein the repetition frequency of the train of optical pulses generated by the first light source is an integral sub-multiple of the repetition frequency of the train of optical pulses generated by the second light source.

In this manner, for example, when it is used for stimulated Raman scattering microscopy, upon the coincidence of the frequency difference between the first optical frequency and the second optical frequency with the molecular vibrational frequency of the sample, stimulated Raman scattering takes place, light scattered from the sample undergoes intensity modulation, and detection of this intensity-modulated component enables molecular vibrational imaging of the sample. This makes it possible to obtain a stimulated Raman scattering-based optical microscope with a simple optical microscope system, in which the modulation frequency of the light pulse trains can be easily set to a high value without using the conventional element used for intensity modulation.

In addition, in the inventive optical microscope, the repetition frequency of the train of optical pulses generated by the first light source preferably is ½ of the repetition frequency of the train of optical pulses generated by the second light source. Doing so makes it possible to obtain an optical microscope that can generate stimulated Raman scattering from the first train of optical pulses and the second train of optical pulses in the most efficient manner and can create better molecular vibrational images of samples.

Furthermore, it preferably comprises the first light source; the second light source; focusing optics that simultaneously irradiate the sample with the first train of optical pulses and the second train of optical pulses; collection optics that remove the first train of optical pulses from the light scattered from the sample and focus the remainder; a light receiving element that converts the scattered light focused by the collection optics into an electrical signal and outputs it; and an electronic circuit that synchronously demodulates the output signal of the light receiving element. This makes it possible readily to implement an optical microscope based on a simple system.

Furthermore, preferably, at least one source among the first light source and the second light source is a fiber laser and the microscope comprises timing difference detection optics that detect the difference in timing between the first train of optical pulses and the second train of optical pulses. The output signal of the timing difference detection optics drives optical path length modulation means disposed inside the resonator of the fiber laser to align the timing of the first train of optical pulses with the timing of the second train of optical pulses. Doing so makes it possible to implement an optical microscope that is capable of aligning the timing of the first train of optical pulses with the timing of the second train of optical pulses with high precision and obtains clear molecular vibrational images with a high S/N ratio.

In addition, the timing difference detection optics preferably detects a two-photon-absorption current generated when condensing the laser beam made up of the first train of optical pulses and the laser beam made up of the second train of optical pulses. In this manner, the timing difference between the ultra-short pulse laser beams of 2 colors can be detected with high precision.

Furthermore, the optical path length modulation means are preferably a variable delay line and a phase modulator. In this manner, more precise timing synchronization that remains stable for long periods of time can be implemented with the help of the variable delay line, which can mechanically adjust the length of the optical path over long distances, and the phase modulator, which can adjust the optical path length at a high speed by changing the refractive index of the crystal using the applied voltage.

Furthermore, the repetition frequency of the train of optical pulses generated by the first light source preferably is 10 MHz or higher, and the repetition frequency of the train of optical pulses generated by the first light source more preferably is 38 MHz or higher.

In addition, the inventive optical microscope is an optical microscope that irradiates a sample with a first train of optical pulses having a first optical frequency and a second train of optical pulses, which has a second optical frequency and is temporally synchronized with the first train of optical pulses, and that detects the light scattered from the sample using a photodiode. In this microscope, a photodiode drive circuit, which acquires the output signal from the photodiode, has an inductor connected in parallel to the photodiode and a load resistor with a resistance value of at least 100Ω connected in parallel to the inductor.

Adopting this type of configuration enables effective prevention of frequency characteristic degradation due to the parasitic capacitance of the photodiode during image detection at a high lock-in frequency.

Furthermore, the present invention relates to optical instrumentation, in which lock-in detection is performed using a first train of optical pulses generated by a first light source and the second train of optical pulses generated by a second light source. In such optical instrumentation, the repetition frequency of the train of optical pulses generated by the first light source is an integral sub-multiple of the repetition frequency of the train of optical pulses generated by the second light source.

Thus, since the first train of optical pulses and the second train of optical pulses with different repetition frequencies used to perform lock-in detection are generated by light sources generating light with different repetition frequencies, optical instrumentation for the purpose of lock-in detection at high frequencies permitting high S/N ratios can be performed using a simple configuration.

Embodiments of the present invention are described below with reference to the drawings.

Embodiment 1

FIG. 1 is a block diagram overview of a stimulated Raman scattering (SRS)-based optical microscope according to the first embodiment of the present invention.

As shown in FIG. 1, the stimulated Raman scattering microscope 100 of this embodiment has: a first light source 1 generating a first train of optical pulses; a second light source 2 generating a second train of optical pulses; focusing optics 21 comprising a mirror 3, a half mirror 4, and a first objective lens 5; collection optics 22 comprising a second objective lens 7, a filter 8, and a focusing lens 9; a photodiode 10, which is a light receiving element; and a lock-in amplifier 11, which is an electronic circuit synchronously demodulating the output signal of the photodiode 10.

In addition, as shown in FIG. 1, a sample to be measured 6 is disposed between the first objective lens 5 and the second objective lens 7.

In the stimulated Raman scattering microscope 100 of this embodiment, a titanium-sapphire laser light source is used as the first light source 1 that generates the first train of optical pulses of the Stokes beam ($\omega_S$). As far as the optical frequency of the laser beam is concerned, the center frequency is set to 1000 nm, the pulse width is 200 fs (femto-seconds), and the repetition frequency is set to 38 MHz.

In addition, in the same manner as the first light source, a titanium-sapphire laser light source with an optical frequency set to an appropriate value of up to about 770 nm, a pulse width of 100 fs, and a repetition frequency of 76 MHz is used as the second light source 2 generating the second train of optical pulses of the anti-Stokes beam ($\omega_{AS}$). The optical frequency of this second train of optical pulses is adjusted as appropriate with regard to the sample under examination such that the frequency difference between it and the optical frequency of the first train of optical pulses coincides with the molecular vibrational frequency of the sample under test.

It should be noted that in the stimulated Raman scattering microscope 100 of this embodiment, respective separate pulsed laser light sources are used as the first light source and the second light source, and these two pulsed laser light sources are connected in electrically order to effect their synchronization. However, the inventive first light source and the second light source are not limited thereto and, for example, it is also possible to use a pulsed laser light source as one of the light sources and a parametric oscillator as the other.

In addition, as described above, in the stimulated Raman scattering-based optical microscope 100 of this embodiment, the repetition frequency of the first train of optical pulses generated in the first light source preferably is ½ of the repetition frequency of the second train of optical pulses generated in the second light source. Below, in this embodiment, the repetition frequency of this first train of optical pulses is designated as "f" and the repetition frequency of the second train of optical pulses is designated as "2f". By doing so, the first train of optical pulses generated in the first light source is generated using timing synchronized at a 1:2 ratio relative to the second train of optical pulses generated in the second optical source. For this reason, the frequency that causes the stimulated Raman scattering effect can be set to the highest possible value in comparison with cases in which the repetition frequency of the first train of optical pulses generated in the first light source is set to e.g. ⅓ or ¼ of the repetition frequency of the second train of optical pulses generated in the second light source, thereby enabling acquisition of molecular vibrational images of samples with greater precision.

However, in the inventive stimulated Raman scattering microscope, setting the repetition frequency of the first train of optical pulses to ½ of the repetition frequency of the second train of optical pulses is not an absolute requirement, and the acquisition of molecular vibrational images of samples based on the stimulated Raman scattering effect can be realized by setting the repetition frequency of the first train of optical pulses to an integral sub-multiple of the repetition frequency of the second train of optical pulses, such as ⅓, ¼, and the like.

In addition, while the embodiment above describes a case wherein the first light pulse train of the two trains of optical pulses, which has a lower repetition frequency, is used as a Stokes beam, the present invention is not limited to such cases, and the first train of optical pulses, which has a lower repetition frequency, also can be used as an anti-Stokes beam.

The second train of optical pulses of the repetition frequency 2f generated in the second light source 2, whose direction is changed by the mirror 3 of the focusing optics 21, is co-axially combined by the half mirror 4 of the focusing optics 21 with the first train of optical pulses of the repetition frequency f generated in the first light source 1. The combined trains of optical pulses are condensed on the sample 6 by the first objective lens 5 of the focusing optics 21. It should be noted that the first objective lens 5 used in this embodiment is a lens with a magnification ratio of ×40 and a numerical aperture (NA) of 0.6.

Thus, if the repetition frequency of the first train of optical pulses, which has a first optical frequency (Color 1), is designated as f and the repetition frequency of the second train of optical pulses, which has a second optical frequency (Color 2), is designated as 2f, then either pulses of 2 colors or pulses of the 2nd color only appear in an alternating manner during each time period of ½f. At such time, stimulated Raman scattering occurs if the frequency difference between the first optical frequency and the second optical frequency coincides with the molecular vibrational frequency of the molecules under examination of the test sample 6, with intensity modulation of frequency f taking place in the excitation optical pulses of the second train of optical pulses only when optical pulses of 2 colors are radiated.

The light scattered from this sample 6 is focused by the second objective lens 7 of the collection optics 22. In the same manner as the first objective lens 5, the second objective lens used in this embodiment is a lens with a magnification ratio of ×40 and a numerical aperture (NA) of 0.6. The short-wave pass filter 8 of the collection optics 22 transmits only the second train of optical pulses from the scattered light focused by the second objective lens 7. After that the pulse train is focused by the focusing lens 9 of the collection optics 22.

The light focused by the focusing lens 9 is photo-electrically converted by the photodiode 10, which is a light receiving element, and outputted as an electrical signal. Synchronous demodulation of the output signal of this photodiode 10 at a lock-in frequency of "f" with the help of the lock-in amplifier 11 makes it possible to detect only the light that is generated by stimulated Raman scattering.

Figure 2:
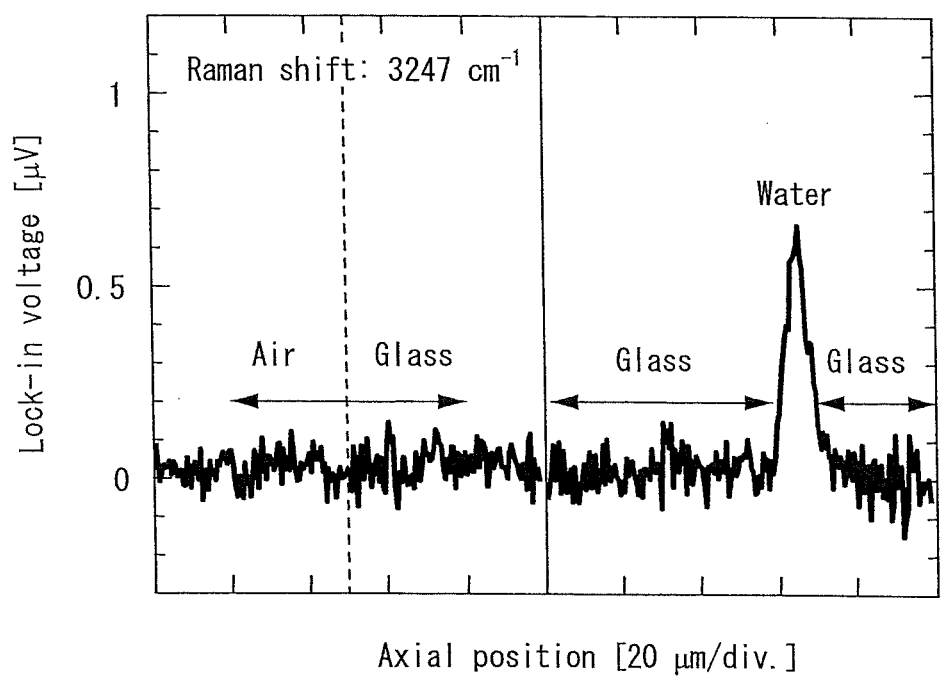
FIG. 2 A diagram illustrating an exemplary stimulated Raman scattering signal obtained by a stimulated Raman scattering microscope.
Figure 3A:
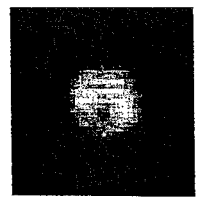
FIGS. 3(a) and (b) are diagrams illustrating molecular vibrational images of polystyrene beads in water, and FIGS. 3(c) and (d) are diagrams illustrating molecular vibrational images of plant cells.
Figure 3B:
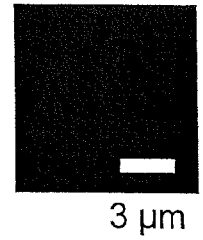
FIG. 3 Illustrates exemplary molecular vibrational images obtained by a stimulated Raman scattering microscope.
Figure 3C:
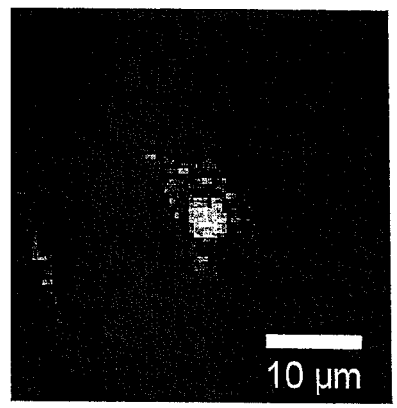
Figure 3D:
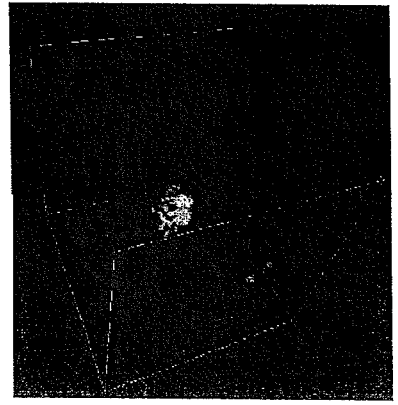

FIG. 2 illustrates an exemplary output signal from a lock-in amplifier in a stimulated Raman scattering microscope.

In FIG. 2, the position of the collection focus of the light obtained by combining the first train of optical pulses and the second train of optical pulses is plotted along the horizontal axis, and the strength of the output signal from the lock-in amplifier obtained at this focal point location is plotted along the vertical axis. It should be noted that the Raman shift value, i.e. the frequency difference ($\omega_{AS}-\omega_S$) obtained by subtracting the value of the first optical frequency of the first train of optical pulses from the value of the second optical frequency of the second train of optical pulses, was 3247 cm$^{-1}$.

The left-hand side of FIG. 2 shows the time course of the output signal obtained when only glass is used as the sample and, as is clearly apparent from FIG. 2, there is no difference between the output signals obtained when the focal point is located in air and when the focal point is located in glass. By contrast, on the right-hand side of FIG. 2, which illustrates the output signal obtained when water between pieces of glass is used as the sample, the output signal voltage obtained when the focal point is in the portion where water is present at the focal point is higher than the one obtained when the focal point is in the glass portion. This shows that while no non-resonant signals are generated in the glass, it is possible to detect the stimulated Raman scattering effect due to the OH vibrational modes of water.

FIG. 3 illustrates exemplary molecular vibrational images obtained based on the stimulated Raman scattering effect with the help of a stimulated Raman scattering microscope.

FIG. 3(*a*), which is a molecular vibrational image obtained when the Raman shift value, i.e. the frequency difference ($\omega_{AS}-\omega_S$), is 3023 cm$^{-1}$, shows a high contrast image, in which only the polystyrene appears white and the signal of the surrounding water is suppressed. At such time, the scan size is 10 μm by 10 μm.

FIG. 3(*b*), which is a molecular vibrational image obtained when the Raman shift value, i.e. the frequency difference ($\omega_{AS}-\omega_S$), in the same sample as in FIG. 3(*a*) is 3228 cm$^{-1}$, has a lower global contrast, with the signal level of the polystyrene bead being lower and the water signal due to OH vibration being somewhat more pronounced.

FIG. 3(*c*) is a visualization of the CH vibrational modes of a plant cell (BY2). FIG. 3(*c*) is a two-dimensional molecular vibrational image obtained by scanning a 40 μm×40 μm range, with a Raman shift value of 3023 cm$^{-1}$. As can be seen, the signal from the water surrounding the cell is minimized, with the nucleus and cell walls clearly visualized.

FIG. 3(*d*) is a three-dimensional molecular vibrational image obtained based on results obtained by acquiring two-dimensional molecular vibrational images such as the one shown in FIG. 3(*c*) at 4-μm intervals across a 40-μm range in the direction of the optical axis. The stimulated Raman scattering microscope of this embodiment allows for three-dimensional molecular vibrational images of the molecular structure of the test sample to be obtained by obtaining multiple two-dimensional molecular vibrational images by shifting the position of the focal point of the emitted beam in this manner in the direction of the optical axis.

In addition, in the stimulated Raman scattering microscope of this embodiment, the changes in the condition of living cells can be captured in the form of video images because molecular states can be detected in real time in the form of molecular vibrational images.

Embodiment 2

Next, explanations will be provided regarding an exemplary configuration of an optical microscope capable of acquiring molecular vibrational images at a high S/N ratio by aligning the timing of the two trains of optical pulses with high precision, which is the stimulated Raman scattering (SRS) effect-based microscope used in the second embodiment of the present invention.

Figure 4:
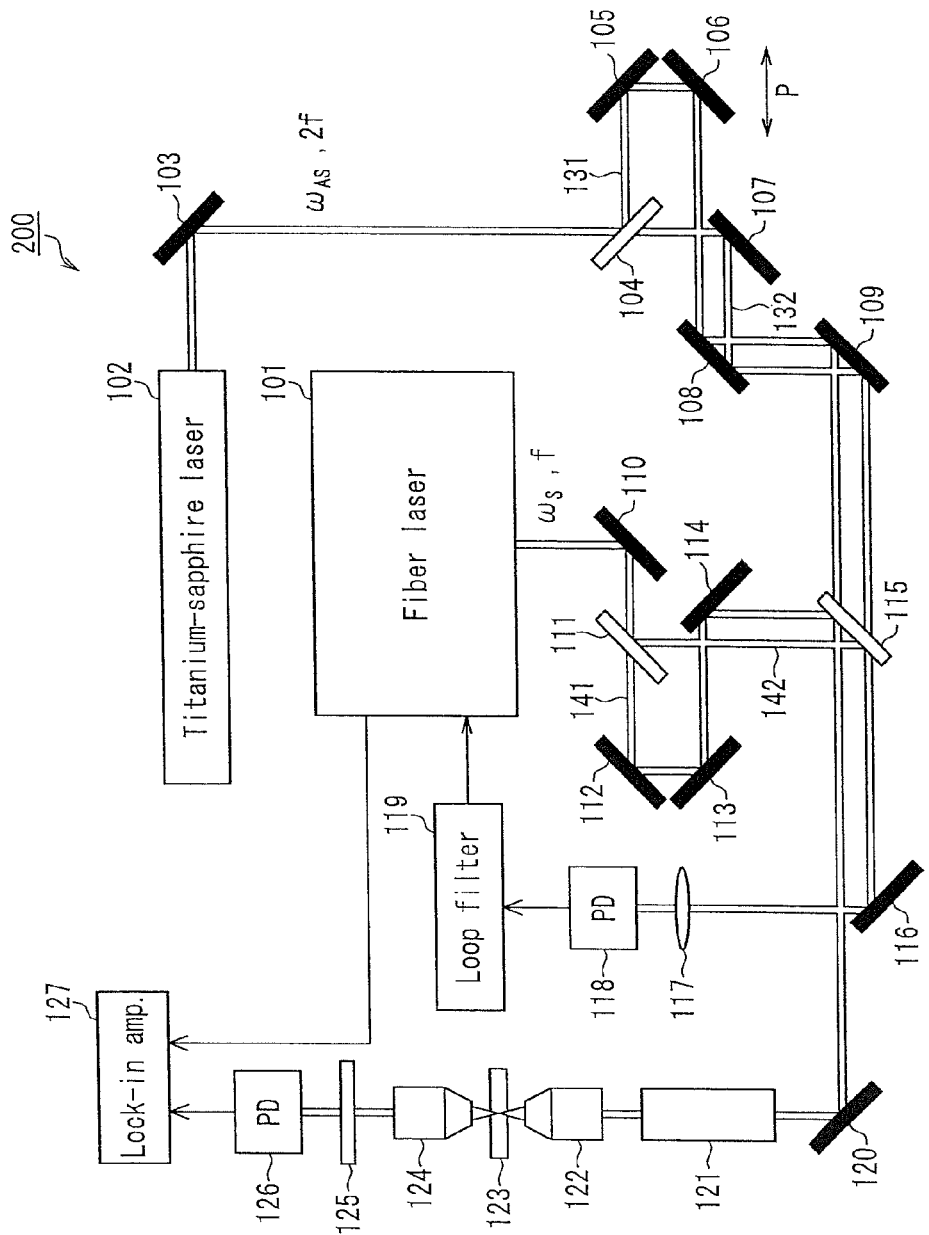
FIG. 4 A block diagram illustrating an overview of the optical microscope according to the second embodiment of the present invention.

FIG. 4 is a block diagram illustrating an overview of the configuration of the optical microscope 200 used in the second embodiment of the present invention.

As shown in FIG. 4, the stimulated Raman scattering-based optical microscope 200 of this embodiment is provided with a fiber laser 101 used as a first light source generating a first train of optical pulses and a titanium-sapphire laser 102 used as a second light source generating a second train of optical pulses. In addition, the optical microscope 200 of this embodiment differs from the optical microscope 100 according to Embodiment 1 explained with reference to FIG. 1 above in that it has a laser beam made up of a first train of optical pulses and timing difference detection optics used for detecting the difference in timing between it and a laser beam made up of a second train of optical pulses.

The ultra-short pulse laser beam made up of the second train of optical pulses emitted from the titanium-sapphire laser 102, which serves as the second light source, is split by the half-mirror 104 into a measuring beam 131, which is used to obtain molecular vibrational images of the sample to be measured 123, and a timing difference detecting beam 132, which is used to detect the difference in timing between it and the ultra-short pulse laser beam made up of the first train of optical pulses emitted from the first light source.

It should be noted that when the timing difference is detected, the position of the mirror 105 and mirror 106 can be adjusted in the direction indicated by the arrow P in the drawing so as to permit adjustment of the optical path length of the measuring beam 131 for the purpose of adjusting the time difference between the timing difference detecting beam 132, which is introduced in the timing difference detection optics, and the measuring beam 131, which irradiates the sample in order to obtain molecular vibrational images of the sample 123.

In the same manner as the second train of optical pulses, the ultra-short pulse laser beam made up of the first train of optical pulses, which is emitted from the fiber laser 101 used as the first light source, is split by a half-mirror 111 into a measuring beam 141, which is used to obtain molecular vibrational images of the sample 123, and a timing difference detecting beam 142, which is used to detect the difference in timing between it and the second train of optical pulses emitted from the second light source.

The timing difference detecting beam 142 made up of the first train of optical pulses, which is emitted from the fiber laser 101, and the timing difference detecting beam 132 made up of the second train of optical pulses, which is emitted from the titanium-sapphire laser 102, are co-axially combined by a dichroic mirror 115 and, upon passing through a lens 117, are condensed in the photodiode 118. In order to detect the two-photon absorption of the combined laser beam, this photodiode 118 preferably is a GaAsP photodiode that e.g. exhibits no light absorption in the near-infrared region, has absorption only in the visible spectrum, and possesses superior high-frequency characteristics. It should be noted that in the present embodiment, the timing difference detection optics are constituted by the lens 117, which condenses the timing difference detecting beam 142 made up of the first train of optical pulses and the timing difference detecting beam 132 made up of the second train of optical pulses, and the photodiode 118, which detects the two-photon-absorption current generated by the two emitted laser beams.

On the other hand, the measuring beam 141 made up of the first train of optical pulses, which is emitted from the fiber laser 101, and the measuring beam 131 made up of the second train of optical pulses, which is emitted from the titanium-sapphire laser 102, are also co-axially combined by the half-mirror 115 and the diameter of the resultant beam is enlarged by a beam expander 121, whereupon the beam enters the pupil of the first objective lens 122, where it is condensed by the same objective lens and emitted to irradiate the sample to be measured 123. Upon passing through a second objective lens 124 and a short-wave pass filter 125, the light scattered from the sample 123 is converted into an electrical signal by a photodiode 126, which is a light receiving element, and the output signal of the photodiode 126 is synchronously demodulated by a lock-in amplifier 127.

In the optical microscope 200 of this embodiment, the laser beam made up of the first train of optical pulses, which is generated by the fiber laser 101, is a Stokes beam ($\omega_S$) with a center wavelength set to an appropriate value of about 1030 nm, a pulse width of 300 fs, and a repetition frequency of 38 MHz. In addition, the laser beam made up of the second train of optical pulses, which is generated by the titanium-sapphire laser 102, is an anti-Stokes beam ($\omega_{AS}$) with a center wavelength set to an appropriate value of about 780 nm, a pulse width of 300 fs, and a repetition frequency of 76 MHz. In the same manner as in the optical microscope of the first embodiment, the wavelengths of the first train of optical pulses and the second train of optical pulses are appropriately adjusted with regard to the sample under test such that the optical frequency difference between them coincides with the molecular vibrational frequency of the sample under test.

In the optical microscope 200 of this embodiment, the use of a titanium-sapphire laser as the second light source, which generates a laser beam made up of the second train of optical pulses with a higher repetition frequency, is due to the fact that it is more difficult to set the repetition frequency to a lower value in a titanium-sapphire laser than in a fiber laser. Accordingly, this is not an absolute requirement in the present invention, and it is possible to use a titanium-sapphire laser as the first light source and a fiber laser as the second light source as may be appropriate depending on the repetition frequencies that are set. In addition, both the first and the second light sources can be fiber lasers.

In addition, the repetition frequency of the first train of optical pulses generated in the first light source is not ½ of the repetition frequency of the second train of optical pulses generated in the second light source and may be simply its integral sub-multiple. In addition, any of the two trains of optical pulses may be a Stokes beam or an anti-Stokes beam. In these respects, the situation is the same as in the case of the stimulated Raman scattering microscope 100 of the first embodiment described above.

Furthermore, the specifications of the optical members, etc., may be the same as in the stimulated Raman scattering microscope 100 of the first embodiment. For example, lenses with a magnification ratio of ×40 and a numerical aperture (NA) of 0.6 can be used as the first objective lens 122 and the second objective lens 124. In addition, a higher spatial resolution can be obtained when using objective lenses with a magnification ratio of (100 and a NA of 1.4.

In FIG. 4, each of the reference numerals 103, 105, 106, 107, 108, 109, 110, 112, 113, 114, 116, and 120 indicates a mirror. Quite naturally, the specific paths of the first and second ultra-short pulse laser beams that use these mirrors can be adjusted appropriately.

Figure 5:
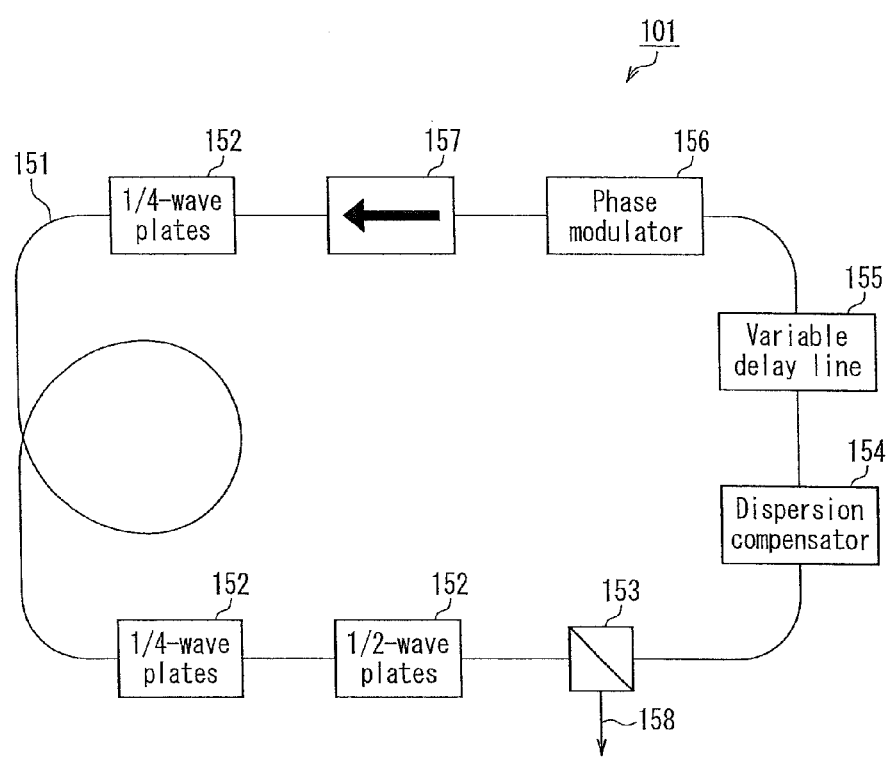
FIG. 5 A block diagram overview of the fiber laser used in the optical microscope according to the second embodiment of the present invention.

FIG. 5 is a block diagram illustrating a specific exemplary configuration of the fiber laser 101 used in the optical microscope 200 of this embodiment.

As shown in FIG. 5, the fiber laser 101, which is used as the first light source in the optical microscope 200 of this embodiment, comprises an Ytterbium-doped fiber 151, multiple wave plates 152, a polarization beam splitter 153, a dispersion compensator 154, a variable delay line 155, a phase modulator 156, and an isolator 157. The configuration of this fiber laser 101 includes optical path length conversion means, i.e. the phase modulator 156 and variable delay line 155, which are introduced into the resonator of a common mode-locked fiber laser.

The ytterbium-doped fiber 151 amplifies optical pulses with a wavelength of 1.03 μm. The multiple wave plates 152 adjust the polarization of light incident on and exiting from the ytterbium-doped fiber 151. Along with emitting some of the optical pulses in the fiber laser 101 as exiting light 158, the polarization beam splitter 153 operates in a mode-locked manner based on non-linear polarization rotation effects in the ytterbium-doped fiber 151. The dispersion compensator 154 is introduced for the purpose of regulating group velocity dispersion in the fiber laser 101.

The variable delay line 155 and phase modulator 156 are introduced in order to adjust the optical path length of the laser resonator and control the repetition frequency. The variable delay line 155 can mechanically adjust the optical path length. In addition, the phase modulator 156 is a waveguide device that uses an electro-optical crystal and can adjust the optical path length by changing the refractive index of the crystal using the applied voltage. Although the maximum optical path length it can adjust is small, on the order of several micron, the phase modulator 156 does not require mechanical operation and can thus control the optical path length at a higher speed of MHz or greater. The isolator 157 specifies the direction of travel of optical pulses inside the resonator.

As a result of generating and circulating of optical pulses in the thus configured fiber laser 101 based on mode-locked operation, optical pulses are outputted at time intervals depending on the optical path length in the laser resonator, thereby making it possible to obtain optical pulses of controlled repetition frequency.

The photocurrent, i.e. the two-photon absorption current, of the photodiode 118 illustrated in FIG. 4, onto which the co-axially combined timing difference detecting beam 142 made up of the first train of optical pulses and timing difference detecting beam 132 made up of the second train of optical pulses are incident, is detected as a voltage value using, e.g., a 300-Ω load resistor, thereby enabling detection at bandwidths of 1 MHz and larger. A sufficiently strong two-photon absorption current has to be obtained at such time in order to suppress the effects of the thermal noise and other fluctuations contained in the detected signal. Co-axially combining the two pulse trains and using a lens with a large numerical aperture, e.g. a lens with a numerical aperture of 0.55 and a magnification ratio of 50, for focusing on the photodiode is effective in doing so.

The voltage signal indicating the detected timing difference was introduced via the loop filter 119 into the variable delay line 155 and phase modulator 156 in the resonator of the fiber laser 101. The loop band of the variable delay line 155 was then controlled to be about 1 Hz and the loop band of the phase 156 was controlled to be about 140 kHz so as to stabilize the above-described voltage signal.

It should be noted that although the optical path length modulation means of the fiber laser employed in the optical microscope 200 of this embodiment, which is illustrated in FIG. 5, were comprised of the variable delay line 155 and phase modulator 156, in the present embodiment this is not an absolute requirement and does not preclude the use of a fiber stretcher or any member capable of changing the optical path length in the resonator of the fiber laser as the optical path length modulation means. However, it is necessary to use high-speed light path length modulation means in order to set the loop band to 100 kHz or higher. For example, it is difficult to increase the loop band to 1 kHz or higher when using only piezo elements as the optical path length modulation means. Since the light pulse train outputted by the fiber laser has an inherently high jitter, a high jitter of about 2 picoseconds remains when timing control is effected using low-speed elements such as piezo elements.

Figure 6:
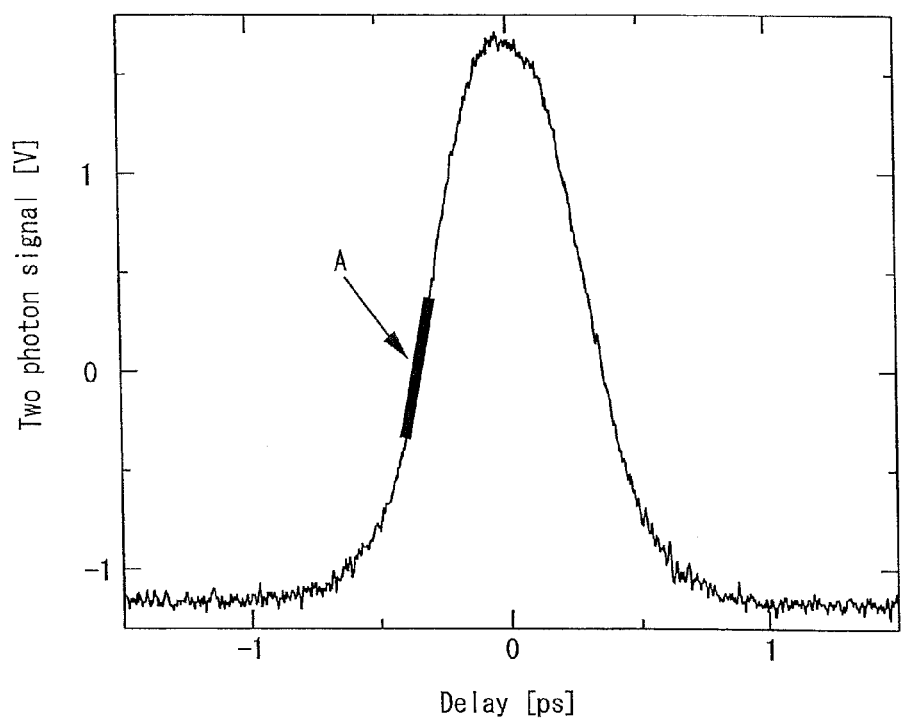
FIG. 6 A diagram illustrating the state of the output signal from the photodiode used in the timing difference detection optics in the optical microscope according to the second embodiment of the present invention.

FIG. 6 illustrates the state of the output signal obtained from the photodiode 118 by the timing difference detection optics used for detecting de-synchronization between the first and second laser beam pulses in the optical microscope 200 of this embodiment.

In FIG. 6, the value of the output voltage of the photodiode 118 resulting from two-photon absorption is plotted along the vertical axis and the magnitude of the timing difference between the two laser beam pulses is plotted along the horizontal axis. The highest voltage is obtained when the timing of the two pulses coincides. In addition, it is apparent that the voltage decreases when the difference in timing is equal to or greater than the pulse width. This provides for highly accurate timing detection based on two-photon absorption.

In the optical microscope 200 of this embodiment, the difference in timing between the laser beam pulses of 2 colors is detected not at Delay=0 shown in FIG. 6, which is the position of the peak, but in the portion designated as "A" in FIG. 6, which has a tilt of about 7 V/ps, thereby making it possible to directly detect the difference in timing between the laser beam made up of the first train of optical pulses, which is generated in the fiber laser 101, and the laser beam made up of the second train of optical pulses based on changes in the output voltage value of the photodiode 118 and use it in controlling the repetition frequency of the fiber laser.

In this manner, the optical microscope 200 of this embodiment avoids the effects of jitter in the ultra-short pulse laser beams and allows for the timing of the ultra-short pulse laser beams of 2 colors to be synchronized with high precision.

In addition, in the optical microscope of this embodiment, widening the band used for controlling the repetition frequency and two-photon absorption current and expanding the loop band makes the synchronization between the two light pulse trains extremely easy. This could be understood as follows.

Changes in the two-photon absorption current occur only when the closeness between the timing of the two light pulse trains is commensurate with the pulse duration $\Delta T$. Here, we consider a case in which the light pulse trains are not synchronized, i.e. there is a difference $\Delta f$ between twice the repetition frequency f of the first train of optical pulses and the repetition frequency 2f of the second train of optical pulses. The repetition frequency of an uncontrolled laser actually exhibits fluctuations on the order of 1 Hz, which can be attributed to the fact that $\Delta f$ varies within approximately 1 Hz over time.

At such time, the timing of the two pulse trains coincides at $1/\Delta f$ time intervals, thereby causing changes in the two-photon absorption current. However, the time when such changes in the two-photon absorption current take place is the time when the timing of the two pulses overlaps, i.e. $\Delta T/T\Delta f$. In order to carry out synchronization, timing control needs to be effected within this time frame.

If we designate the timing control frequency range as B, then the time required for timing synchronization will be approximately $1/B$ and the inequality $1/B<\Delta T/T\Delta f$, i.e. $\Delta f<B\Delta T/T$, should therefore be satisfied. If $\Delta T$ is 300 fs, T is 12 ns, and B is 140 kHz, then $\Delta f<3.5$ Hz. Therefore, increasing the timing control frequency range in this manner makes it possible to achieve two-photon absorption-based synchronization even in the presence of fluctuations on the order of 1 Hz. On the other hand, when B is small, stringent requirements are imposed on $\Delta f$, and it becomes practically impossible to synchronize an uncontrolled laser. In such a case, two-photon absorption based synchronization is performed after concomitantly using other synchronization methods to perform low-grade synchronization, which makes the system more complicated.

Figure 7:
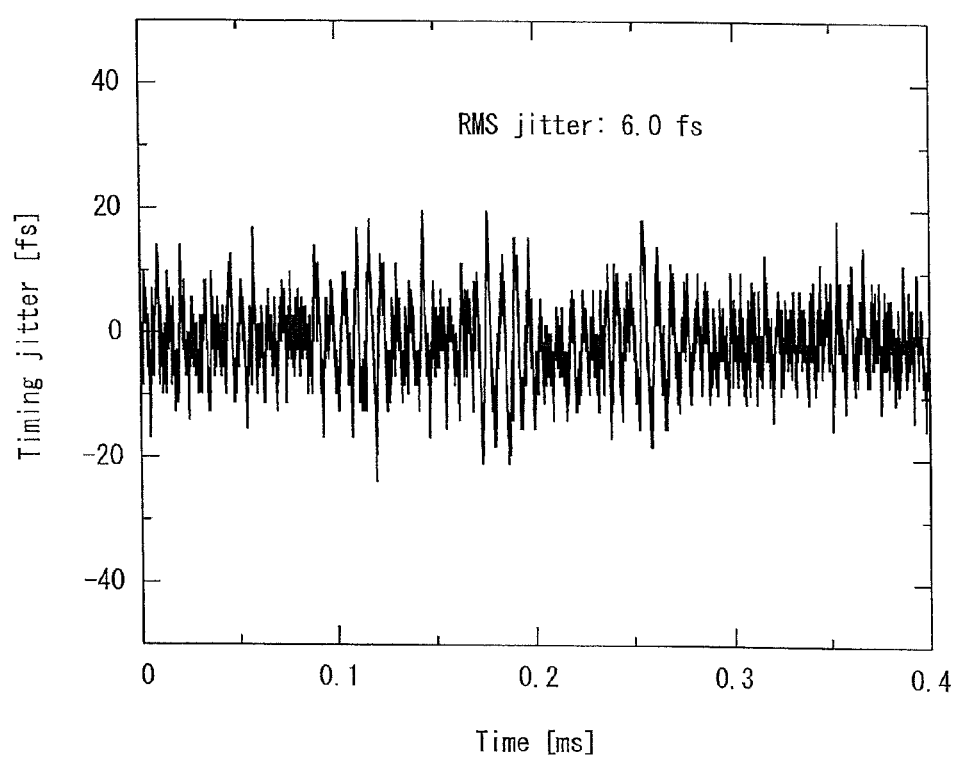
FIG. 7 A diagram illustrating the synchronization status of the ultra-short pulse laser beams of 2 colors in the optical microscope according to the second embodiment of the present invention.

FIG. 7 is a diagram illustrating the synchronization status of the ultra-short pulse laser beams of 2 colors in the optical microscope 200 according to this embodiment.

As shown in FIG. 7, in the optical microscope 200 of this embodiment, the timing jitter, which is obtained as a deviation of the ultra-short pulse laser beams of 2 colors, can be set to about 6.0 fs. Although it is generally believed that it is preferable to reduce timing jitter to 1/10 of the duration of the irradiation beam pulses when molecular vibrational images are observed in an SRS microscope, the magnitude of timing jitter implemented in the optical microscope 200 of this embodiment constitutes 11100 of the duration of the irradiation beam pulses.

As explained above, in the optical microscope 200 of this embodiment, 2-photon absorption is detected using a simple configuration, without complicating the measuring system in the way it is complicated when using high-speed optical detectors to detect differences in timing, and, at the same time, controlling the repetition frequency of the fiber laser with the help of a phase modulator at high speed makes it possible to obtain molecular vibrational images with a high S/N ratio and with a high level of sensitivity based on suppressing the effects of timing jitter.

It should be noted that while the above-mentioned second embodiment of the present invention described detection of a two-photon absorption current generated by the laser beam made up of the first train of optical pulses and the laser beam made up of the second train of optical pulses in the timing difference detection optics, this does not constitute a limitation upon the timing difference detection optics of the optical microscope of the present invention. For example, the timing difference detection optics can detect the difference in timing between the ultra-short pulse laser beams of 2 colors using sum frequency generation.

As described above, in the optical microscope of the present invention, that stimulated Raman scattering phenomenon that takes place when a sample is irradiated with light pulse trains of 2 colors (optical frequencies: $\omega_{AS}$, $\omega_S$), among which one light pulse train has a repetition frequency that is an integral sub-multiple of the other, and the frequency difference between the 2 colors coincides with the molecular vibrational frequency of the sample at the focal point, makes it possible to detect the intensity modulated part of the excitation optical pulses that have a higher repetition frequency. Since such stimulated Raman scattering is not subject to non-linear electron effects, there are no background signals in the output signal obtained in this microscope, which makes it possible to obtain high-contrast molecular vibrational images.

In addition, in this microscope, setting the repetition frequency of one of the light pulse trains of 2 colors to an integral sub-multiple of the other makes it unnecessary to use an acoustro-optic modulator in order to intensity-modulate one of the light pulse trains, thereby making it possible to simplify the system of the optical microscope and enabling advantageous high-frequency modulation of the irradiation beam based on laser intensity noise reduction and video image acquisition. This makes it possible to implement an optical microscope with a simplified system capable of obtaining high quality video images with a high S/N ratio, i.e. signal-to-noise ratio.

Here, explanations will be provided regarding the relationship between the lock-in frequency and the resultant molecular vibrational images in the stimulated Raman scattering microscope.

FIG. 8 and FIG. 9 are both molecular vibrational images of samples obtain using a stimulated Raman scattering microscope.

In FIG. 8, a polystyrene bead embedded in water is used as a sample. FIG. 8(a) is a molecular vibrational image obtained when the lock-in frequency is 2 MHz, and FIG. 8(b) is a molecular vibrational image obtained when the lock-in frequency is 10 MHz. It should be noted that the optical power used when obtaining the molecular vibrational image of FIG. 8(a) was 5 mW The integration time required for obtaining the molecular vibrational image was 50 ms. In addition, the optical power used when obtaining the molecular vibrational image of FIG. 8(b) was 0.6 mW. The integration time required for obtaining the molecular vibrational image was 2 ms.

The resolution of the molecular vibrational image of FIG. 8(a), which has a lower lock-in frequency, is clearly lower than that of the molecular vibrational image of FIG. 8(b), which has a higher lock-in frequency. The area surrounding the resultant image is out of focus, which makes the diameter of the bead appear larger. In addition, the higher the lock-in frequency, the smaller the beam irradiation power required for obtaining the molecular vibrational image and the smaller the burden on the beam irradiation system. Furthermore, it can be seen that the time required for obtaining the molecular vibrational image is shortened, which makes it more suitable for obtaining video images.

In FIG. 9, a plant cell (BY2) was used as a sample. FIG. 9(a) is a molecular vibrational image obtained when the lock-in frequency is 2 MHz, and FIG. 9(b) is a molecular vibrational image obtained when the lock-in frequency is 10 MHz. The optical power used when obtaining the molecular vibrational image of FIG. 9(a) was 4.5 mW and the integration time required to obtain the molecular vibrational image was 100 ms. The optical power used when obtaining the molecular vibrational image of FIG. 9(b) was 1 mW and the integration time required for obtaining the molecular vibrational image was 3 ms.

In the same manner as in FIG. 8, the molecular vibrational images of FIG. 9(a) and FIG. 9(b) show that the higher the lock-in frequency, the higher the signal-to-noise ratio of the resultant molecular vibrational images. In addition, the images have excellent contrast and the detailed configuration of the plant cell can be easily understood. In addition, the data obtained from FIG. 9(a) and FIG. 9(b) show that the higher the lock-in frequency, the smaller the optical power and integration time required for obtaining the molecular vibrational images.

Based on the above, it is clear that in the stimulated Raman scattering microscope described in this embodiment it is preferable to set the lock-in frequency to 10 MHz or higher in order to obtain molecular vibrational images of a constant resolution. To set the lock-in frequency to 10 MHz or higher, it is sufficient to set the repetition frequency of the light pulse train with a lower repetition frequency to 10 MHz and the repetition frequency of the light pulse with a higher repetition frequency to 20 MHz. In addition, when the lock-in frequency is set to 10 MHz or higher, the optical power necessary for obtaining the molecular vibrational images may be set to about 1 mW. If such optical power is used, no significant burden is imposed on the beam irradiation system. Furthermore, when the lock-in frequency is set to 10 MHz or higher, the integration time required for obtaining the molecular vibrational images is several ms, which is preferable in terms of acquiring video images.

Figure 10:
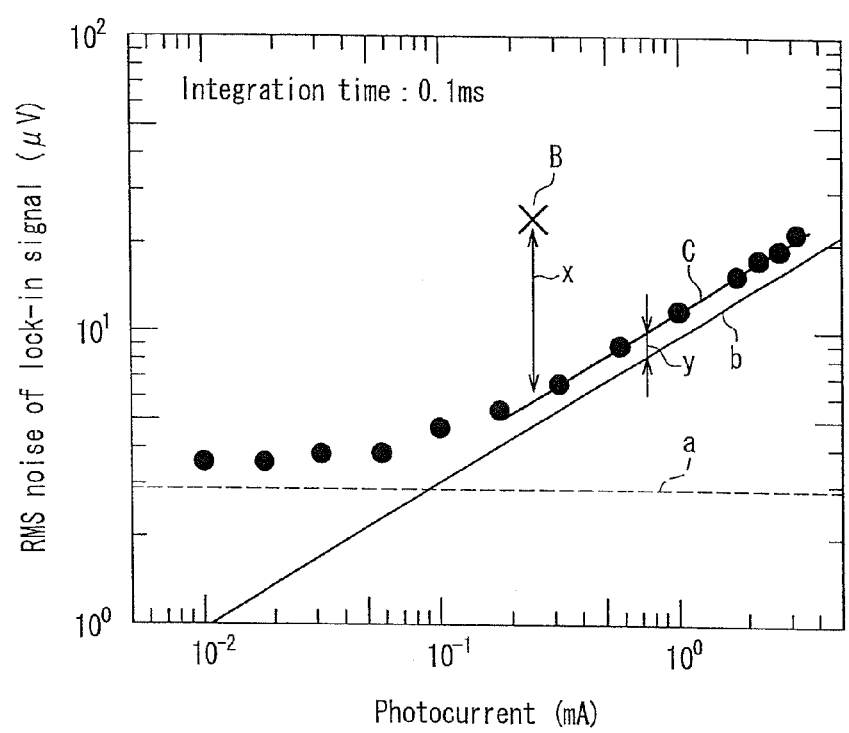
FIG. 10 A diagram illustrating the relationship between the lock-in frequency and magnitude of noise in molecular vibrational images obtained by the optical microscope according to the second embodiment of the present invention.

Next, FIG. 10 will be used to describe the relationship between the level of the noise contained in the lock-in signal obtained by the stimulated Raman scattering microscope described in this embodiment and the magnitude of the output current obtained in the photodiode, which operates as an image receiving unit.

FIG. 10 illustrates results obtained by measuring the noise component of the lock-in signal obtained in the optical microscope 200 illustrated in the second embodiment described above. The "black dots" shown in FIG. 10 represent a plot of the measurement results data.

When the titanium-sapphire laser 102 and fiber laser 101 in the optical microscope 200 illustrated in FIG. 4 were synchronized, only the light of the titanium-sapphire laser was introduced into the photodiode 126. At such time, the light of the fiber laser was removed by the optical filter 125. The output signal of the photodiode 126 was supplied to the lock-in amplifier 127 and the electrical signal with a repetition frequency of 38 MHz obtained from the fiber laser was used as a reference signal of the lock-in amplifier 127.

The plot of FIG. 10 represents the results obtained by measuring the output noise of the lock-in amplifier 127 while changing the intensity of the light supplied to the photodiode 126. It should be noted that the integration time of the lock-in amplifier 127 was 0.1 ms.

In FIG. 10, the horizontal axis represents the DC component of the photocurrent obtained from the photodiode 126. In addition, the noise level of the light receiving circuit of the photodiode 126 is designated with the dotted line "a" and the shot noise of the photodiode 126 calculated from the photocurrent is designated by the solid line "b".

As can be seen from FIG. 10, the noise of the circuit prevails in the region where the photocurrent value is smaller than $10^{-1}$ mA, but as the photocurrent becomes stronger, the noise increases. Here, when the light of the titanium-sapphire laser exhibits excessive noise higher than the shot noise, the noise voltage of the lock-in signal is proportionate to the photocurrent. In addition, when the light of the titanium-sapphire laser exhibits low-noise properties in terms of the shot noise limit, the noise voltage of the lock-in signal is proportionate to the square root of the photocurrent.

In the experiments, the noise voltage of the lock-in signal was proportionate to the square root of the photocurrent in the region, in which the value of the photocurrent was 0.2 mA or higher, pointing to low-noise properties in terms of the shot noise limit. It should be noted that there is a difference of about 1.6 dB between the solid line "c" of the plot in the region where the photocurrent value is 0.2 mA or higher and the solid line "b" indicating the theoretical value of the shot noise, which is designated as "y" in the figure, but this difference is assumed to be due to losses in the bandpass filter circuit contained in the photo-detection circuit.

In addition, in a system in which optical pulses with a repetition frequency of 76 MHz were obtained using a titanium-sapphire laser and an optical parametric oscillator and the latter were subjected to 10.7 MHz optical modulation using an optical modulator in order to perform lock-in detection, the noise of the lock-in signal was converted to the current test conditions and the results are shown as X (B) in the figure.

As can be seen from FIG. 10, in comparison with the conventional noise level B, increasing the magnitude of the lock-in frequency to 38 MHz permitted a noise level suppression of 12 dB or more as indicated by the symbol "x" in the figure. These results confirmed the effectiveness of noise reduction based on increasing the magnitude of the lock-in frequency. As is apparent from the experimental data of FIG. 10, setting the lock-in frequency to 38 MHz makes it possible to reduce the noise level of the lock-in signal to the shot noise level of the photodiode 126 used as the light receiving element and, therefore, setting the lock-in frequency to 38 MHz or higher makes it possible to acquire molecular vibrational images with extremely low noise levels.

Also, it is understood that, as confirmed by the actual acquired molecular vibrational images and experimental data concerning noise levels, higher lock-in frequencies make it possible to obtain sharper molecular vibrational images within a shorter time period. While this is particularly advantageous in terms of acquiring video images, i.e. molecular vibrational images in the form of video, the average level of the optical power used to irradiate the sample imposes limitations on the acquisition of molecular vibrational images by the photodiode and setting the lock-in frequency to an excessively high value may result in damage to the sample by the injected optical energy. For this reason, when setting the lock-in frequency, it is preferable to set the upper limit value appropriately, taking account into the capacity of the light-receiving circuitry, so as not to exceed the limit at which damage to the sample may occur.

Figure 11:
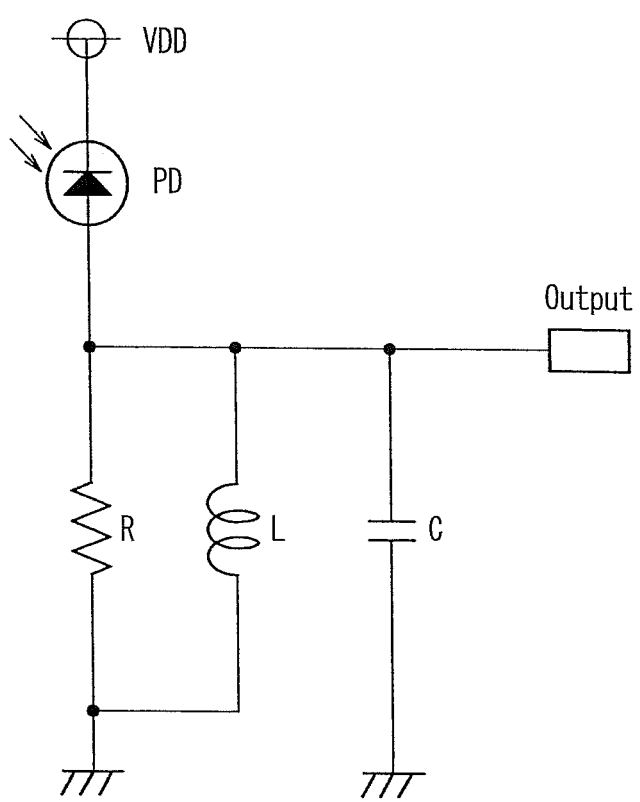
FIG. 11 A block diagram illustrating the circuit configuration of the photodiode drive circuit used in the optical microscope according to the second embodiment of the present invention.
Figure 12:
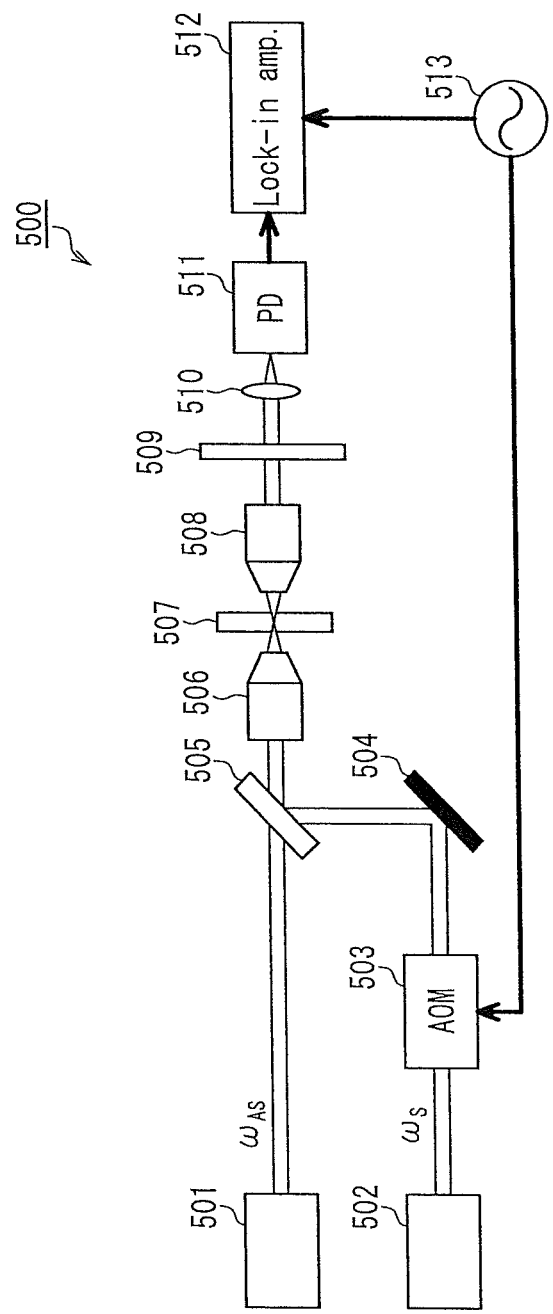
FIG. 12 A block diagram illustrating an overview of a conventional stimulated Raman scattering microscope.

It should be noted that when the data of FIG. 10 was obtained, the circuit illustrated in FIG. 11 was used as the light receiving circuit of the photodiode 126 in order to reduce the noise level (dotted line "a" in FIG. 10) of the light receiving circuit.

As shown in FIG. 11, in order to suppress frequency characteristic degradation caused by the parasitic capacitance of the photodiode PD, in the light receiving circuit used for noise level reduction, an inductor L was connected in parallel to the photodiode PD and the value of the load resistor R connected in parallel to the inductor L was made higher than the load resistance value of 50Ω commonly used in high frequency circuits.

In an exemplary circuit used for acquiring the data of FIG. 10, the parasitic capacitance of the photodiode PD was 20 pF, the inductance L was 820 nH, and the resistance value of the load resistor R was 500Ω. While photodiodes (PD) used in stimulated Raman scattering microscopes tend to have a large light receiving area and a large parasitic capacitance, in the optical microscope 200 of this embodiment, the above-described measures applied to the light receiving circuit allowed for the noise level to be reduced. It should be noted that a value of 100Ω or higher is believed to be preferable as the value of the load resistance R at such time. Accordingly, it is preferable to set the value of the load resistance to an appropriate value of 100 Ohm or higher with account taken of the value of the inductance L used and the numerical value of the parasitic capacitance of the photodiode PD.

In addition, the effects of suppressing the degradation of the frequency characteristics of the photodiode PD, which are due to the use of the circuit illustrated in FIG. 11 as the light receiving circuit of the photodiode PD, do not depend on the generation of the light pulse trains used to irradiate the sample. For this reason, the light receiving circuit of the photodiode PD illustrated in FIG. 11 can be used not only in optical microscopes, in which the light pulse train of the first repetition frequency and the light pulse train of the second repetition frequency are generated by different light sources, such as the ones described in the embodiments of the present invention above, but also in conventional optical microscopes, in which one of the light pulse trains is generated by modulating the other, such as the ones described in Non-patent Document 1 and Non-patent Document 2, and its use there can be extremely efficient.

As discussed above, it is understood that increasing the lock-in frequency is extremely effective in obtaining molecular vibrational images of higher resolution in the optical microscope of this embodiment. Using the optical microscope of the present invention makes it possible easily to address the issue of increasing in the lock-in frequency by generating the repetition frequencies of the light pulse trains of two colors using two light sources one of which has a repetition frequency that is an integral sub-multiple of the other. For this reason, the optical microscope of the present invention is characterized by superior practical features, such as the fact that in this microscope the system of the optical microscope can be simplified in comparison with conventional stimulated Raman scattering microscopes, which require modulators, such as acoustro-optic modulators, the fact that it can obtain molecular vibrational images with a high S/N ratio because the intensity noise of the laser can be reduced, and, furthermore, the fact that it is more advantageous for video image acquisition.

In the embodiments described above, the descriptions of the optical microscope of the present invention focused on microscopes used for the detection of stimulated Raman scattering. However, the use of the configuration of the present invention for detection purposes is not limited to the abovementioned stimulated Raman scattering. For example, in addition to the above, selecting the wavelength of the optical pulses of two colors such that the sum frequency $\omega_{AS}+\omega_S$ of the optical pulses coincides with the two-photon absorption frequency of the sample makes it possible to obtain two-photon absorption images with a high level of contrast.

In addition, the applications of the present invention, as described in the embodiments above, were limited to optical microscopes. However, rather than using the method, in which generation of a first train of optical pulses having a repetition frequency that is an integral sub-multiple of the repetition frequency of a second train of optical pulses is carried out by setting the repetition frequency to an integral sub-multiple by modulating one of two light pulse trains with identical repetition frequencies, the method of the present invention employs two light sources, in which the repetition frequency of the light pulse train generated by one of the sources is an integral sub-multiple of the repetition frequency of the light pulse train generated by the other, and, as a result, makes it possible to perform lock-in detection at higher frequencies using a simpler configuration.

Therefore, the technical idea of the present invention is not limited to applications geared towards optical microscopes. As a result of performing lock-in detection at high frequencies, the noise component contained in the measurement results is reduced and measurement results with a high S/N ratio are obtained. For this reason, the invention can produce excellent results when applied to various types of optical instrumentation. It should be noted that pump probe measurements etc. can be contemplated as the type of optical instrumentation, to which the technical idea of the present invention can be applied.

INDUSTRIAL APPLICABILITY

As discussed above, the optical microscope of the present invention is expected to find a wide range of applications in optical microscopy that enables imaging of living cells and the like. In addition, the present invention can be applied to various types of optical instrumentation.

The invention claimed is:

1. An optical microscope comprising:
a first light source configured to irradiate a sample with a first train of optical pulses having a first optical frequency;
a second light source configured to irradiate the sample with a second train of optical pulses having a second optical frequency, which is temporally synchronized with the first train of optical pulses;
a light receiving element configured to convert light scattered from the sample into an electrical signal, the light scattered from the sample being caused by the first and second light sources irradiating the sample with the first and second trains of optical pulses; and
a lock-in amplifier configured to synchronously demodulate the electrical signal of the light receiving element using a first repetition frequency of the first train of optical pulses as lock-in frequency,
wherein the first repetition frequency of the first train of optical pulses is an integral sub-multiple of a second repetition frequency of the second train of optical pulses.

2. The optical microscope according to claim 1, wherein the first repetition frequency is ½ of the second repetition frequency.

3. The optical microscope according to claim 1, further comprising:
focusing optics configured to simultaneously irradiate the sample with the first train of optical pulses and the second train of optical pulses; and
collection optics configured to remove the first train of optical pulses from the light scattered from the sample and for focusing the remainder to the light receiving element.

4. The optical microscope according to claim 3, wherein:
at least one of the first light source or the second light source is a fiber laser having a resonator, and
the optical microscope further comprises:
timing difference detection optics configured to detect a difference in timing between the first train of optical pulses and the second train of optical pulses, and configured to convert the detected difference into an output signal; and
an optical path length modulator disposed inside the resonator of the fiber laser is driven to align the timing of the first train of optical pulses with the timing of the second train of optical pulses based on the output signal of the timing difference detection optics.

5. The optical microscope according to claim 4, wherein the timing difference detection optics is configured to detect two-photon-absorption current generated when the first train of optical pulses and the second train of optical pulses are condensed and used for irradiation.

6. The optical microscope according to claim 4, wherein the optical path length modulator comprises a variable delay line and a phase modulator.

7. The optical microscope according to claim 1, wherein the lock-in amplifier detects the second train of optical pulses that are intensity-modulated due to a stimulated Raman scattering caused by irradiating the sample with the first and second trains of optical pulses.

8. The optical microscope according to claim 1, wherein the first and second light sources are controlled so that a frequency difference between the first and second optical frequencies coincides with a molecular vibrational frequency of the sample.

9. The optical microscope according to claim 1, wherein the first and second light sources are controlled so that a sum frequency of the first and second optical frequencies coincides with a two-photon absorption frequency of the sample.

10. An optical microscopy method comprising the steps of:
irradiating a sample with a first train of optical pulses having a first optical frequency, which is generated by a first light source, and a second train of optical pulses having a second optical frequency, which is temporally synchronized with the first train of optical pulses and is generated by a second light source;
converting light scattered from the sample into an electrical signal, the light scattered from the sample being caused by the first and second light sources irradiating the sample with the first and second trains of optical pulses; and synchronously demodulating the electrical signal using a first repetition frequency of the first train of optical pulses as a lock-in frequency, wherein the first repetition frequency of the first train of optical pulses is an integral sub-multiple of a second repetition frequency of the second train of optical pulses.

11. The optical microscopy method according to claim 10, wherein the first repetition frequency is ½ of the second repetition frequency.

12. The optical microscopy method according to claim 10, further comprising the steps of:
   simultaneously irradiating the sample with the first train of optical pulses and the second train of optical pulses; and
   removing the first train of optical pulses from the light scattered from the sample and focusing the remainder.

13. The optical microscopy method according to claim 12, wherein:
   at least one of the first light source or the second light source is a fiber laser, and
   the method comprises the steps of:
   detecting a difference in timing between the first train of optical pulses and the second train of optical pulses; and
   based on the detected difference in timing, aligning the timing of the first train of optical pulses with the timing of the second train of optical pulses.

14. The optical microscopy method according to claim 13, further comprising the steps of detecting two-photon-absorption current generated when the first train of optical pulses and the second train of optical pulses are condensed and used for irradiation.

* * * * *